United States Patent
Nakashima et al.

(10) Patent No.: US 12,297,380 B2
(45) Date of Patent: May 13, 2025

(54) METHOD FOR PRODUCING ADHESIVE LAYER COMPOSITION FOR PRODUCING COOLING SHEET, METHOD FOR PRODUCING COOLING SHEET, AND COOLING SHEET

(71) Applicant: HISAMITSU PHARMACEUTICAL CO., INC., Tosu (JP)

(72) Inventors: Kentaro Nakashima, Tosu (JP); Kento Ichinohe, Tosu (JP); Keiichiro Tsurushima, Tosu (JP); Takaaki Yoshinaga, Tosu (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 485 days.

(21) Appl. No.: 17/798,412

(22) PCT Filed: Feb. 4, 2021

(86) PCT No.: PCT/JP2021/004144
§ 371 (c)(1),
(2) Date: Aug. 9, 2022

(87) PCT Pub. No.: WO2021/161895
PCT Pub. Date: Aug. 19, 2021

(65) Prior Publication Data
US 2023/0093050 A1 Mar. 23, 2023

(30) Foreign Application Priority Data

Feb. 12, 2020 (JP) .................... 2020-021577

(51) Int. Cl.
| C09J 133/02 | (2006.01) |
| C09J 7/30 | (2018.01) |
| C09J 11/06 | (2006.01) |
| C09J 11/08 | (2006.01) |

(52) U.S. Cl.
CPC ........... *C09J 133/02* (2013.01); *C09J 7/30* (2018.01); *C09J 11/06* (2013.01); *C09J 11/08* (2013.01); *C09J 2203/358* (2020.08)

(58) Field of Classification Search
CPC ... C09J 133/02; C09J 7/385; C09J 7/30; C09J 11/06; C09J 11/08; C09J 2423/00; C09J 2301/408; C09J 2203/358; C09J 2433/00; C09J 2429/00; C09J 2401/00; A61F 7/10; A61F 7/08; A61F 2007/0052; A61F 2007/0226; C08L 29/04; C08L 33/02; C08L 1/286; C08K 5/175; C08K 2003/3081

See application file for complete search history.

(56) References Cited

U.S. PATENT DOCUMENTS

| 6,207,184 | B1 | 3/2001 | Ikeda et al. | |
| 2002/0193026 | A1* | 12/2002 | Ota | A61F 7/02 442/268 |
| 2014/0302118 | A1 | 10/2014 | Kawamura et al. | |
| 2022/0125626 | A1* | 4/2022 | Nakashima | C08K 5/12 |

FOREIGN PATENT DOCUMENTS

| EP | 1 317 933 A1 | 6/2003 | |
| EP | 1 568 366 A1 | 8/2005 | |
| EP | 2 735 308 A1 | 5/2014 | |
| JP | 59-110617 A | 6/1984 | |
| JP | 2000-007559 A | 1/2000 | |
| JP | 2005-154414 A | 6/2005 | |
| JP | 2009-073777 A | 4/2009 | |
| JP | 2009-155434 A | 7/2009 | |
| JP | 2011-012015 A | 1/2011 | |
| JP | 2017-008024 A | 1/2017 | |
| JP | 2024543282 A * | 11/2024 | ............ C09J 123/14 |
| WO | 2013/027840 A1 | 2/2013 | |

OTHER PUBLICATIONS

International Search Report for PCT/JP2021/004144 dated Apr. 13, 2021.
International Preliminary Report on Patentability dated Aug. 11, 2022 with a Translation of the Written Opinion of the International Searching Authority in Application No. PCT/JP2021/004144.
Extended European Search Report dated Feb. 21, 2024 in Application No. 21752954.4.

* cited by examiner

*Primary Examiner* — Carlos N Lopez
(74) *Attorney, Agent, or Firm* — Sughrue Mion, PLLC

(57) ABSTRACT

A method for producing an adhesive layer composition for producing a cooling sheet including a backing layer, an adhesive layer, and a liner layer, the method comprising the step of:
  mixing a composition to be mixed containing water, an alum, sodium edetate, a polyacrylic acid, and a neutralized polyacrylic acid such that a mixing temperature becomes 5 to 23° C., to obtain an adhesive layer composition, wherein
  in the composition to be mixed,
  a content of the water is 69 to 938.24% by mass relative to a total mass of the composition to be mixed,
  a content of the alum is 0.18 to 0.42% by mass relative to the total mass of the composition to be mixed,
  a content of the sodium edetate is 0.08 to 0.18% by mass relative to the total mass of the composition to be mixed, and
  a mass ratio between the content of the alum and the content of the sodium edetate (the content of the alum: the content of the sodium edetate) is 1:1 to 5.25:1.

10 Claims, No Drawings

METHOD FOR PRODUCING ADHESIVE LAYER COMPOSITION FOR PRODUCING COOLING SHEET, METHOD FOR PRODUCING COOLING SHEET, AND COOLING SHEET

CROSS REFERENCE TO RELATED APPLICATIONS

This application is a National Stage of International Application No. PCT/JP2021/004144 filed Feb. 4, 2021, claiming priority based on Japanese Patent Application No. 2020-021577 filed Feb. 12, 2020.

TECHNICAL FIELD

The present invention relates to a method for producing an adhesive layer composition for producing a cooling sheet, a method for producing a cooling sheet, and a cooling sheet, and more specifically relates to a method for producing an adhesive layer composition for producing a cooling sheet including a backing layer, an adhesive layer, and a liner layer, a method for producing a cooling sheet using the same, and a cooling sheet obtained by these.

BACKGROUND ART

Cooling sheets for comfortably cooling applied sites of human bodies, clothes, and the like have conventionally been known, and as such a cooling sheet, for example, Japanese Unexamined Patent Application Publication No. 2000-7559 (PTL 1) describes an aqueous patch including an aqueous adhesive containing 0.05 to 10% by weight of a copolymer of a (meth)acrylic acid aminoalkyl ester and a (meth)acrylic acid alkyl ester.

In addition, as the cooling sheet, it is known to use a woven fabric or a braided fabric as a backing, and for example, Japanese Unexamined Patent Application Publication No. 2005-154414 (PTL2) describes a member for external use on skin having an adhesive surface obtained by applying or spreading a water-containing adhesive onto a base fabric, or coating or impregnating the base fabric with the water-containing adhesive, the base fabric being formed by knitting, in double-sided stockinette of two or more stages, a multifilament yarn of a thermoplastic synthetic resin subjected to a crimping process.

Furthermore, for example, International Publication No. 2013/027840 (PTL 3) describes a water-containing patch including a backing and an adhesive layer arranged on the backing, wherein a hydrophilic adhesive and diethylene glycol or a diethylene glycol monoalkyl ether are blended in the adhesive layer, as a water-containing patch aiming to make it easy to uniformly apply an adhesive containing lidocaine.

However, although in cooling sheets of a type in which a water-soluble polymer, water, and the like are blended in an adhesive layer which comes into direct contact with an applied site, the cooling action and the cooling duration action thereof are generally exhibited by increasing the water content, these conventional aqueous adhesive, water-containing adhesive, adhesive layer, and the like have still not had sufficient water contents.

On the other hand, for example, Japanese Unexamined Patent Application Publication No. 2009-155434 (PTL 4) describes swelling a high water-absorption resin compound with water in advance to form a water-containing product of the high water-absorption resin compound, and forming a water-containing adhesive in which the water-containing product is dispersed in an adhesive base agent phase containing a water-soluble polymer compound for the purpose of providing a water-containing patch having high water content, high adhesiveness, and high shape retention and being excellent in maintenance of the cooling effect. However, the water-containing adhesive described in PTL 4 has problems that it is necessary to use a high absorption resin compound and that the production method requires a large number of steps.

CITATION LIST

Patent Literature

[PTL 1] Japanese Unexamined Patent Application Publication No. 2000-7559
[PTL 2] Japanese Unexamined Patent Application Publication No. 2005-154414
[PTL 3] International Publication No. 2011/027840
[PTL 4] Japanese unexamined Patent Application Publication No. 2009-155434

SUMMARY OF INVENTION

Technical Problem

The present inventors investigated, for a cooling sheet of a type in which a water-soluble polymer, water, and the like are contained in an adhesive layer which comes into direct contact with an applied site, to further increase the content of water in the adhesive layer for the purpose of further enhancing cooling performance such as cooling power and cooling duration. As a result, the present inventors have found that when the content of water of an adhesive layer composition for forming the adhesive layer is increased (for example, 69% by mass or more), this causes problems that seepage of the adhesive layer becomes more likely to occur during the storage and use of the obtained cooling sheet, and the like. On the other hand, the present inventors have found that if the content of the water-soluble polymer is increased in order to suppress the occurrence of seepage of the adhesive layer, this causes a problem that spread unevenness occurs in the obtained adhesive layer because the water-soluble polymer cannot be evenly spread. Note that the "seepage" of the adhesive layer herein means a phenomenon that the adhesive layer itself is fluidized and passes through an abutting backing layer (for example, a fabric or the like), and part or all of the adhesive layer oozes out onto a surface of the backing layer opposite to the adhesive layer.

The present invention has been made in view of the above-described problems found by the present inventors, and has an object to provide a method for producing an adhesive layer composition that allows production of a cooling sheet of the type in which water-soluble polymer, water, and the like are contained in an adhesive layer which comes into direct contact with an applied site, the cooling sheet having a sufficiently high water content and allowing occurrence of spread unevenness and seepage of the adhesive layer to be sufficiently suppressed, a method for producing a cooling sheet using the same, and a cooling sheet obtained by these.

Solution to Problem

As a result of conducting earnest studies in order to achieve the above object, and the present inventors have found that when an adhesive layer composition for producing a cooling sheet of a type in which a water-soluble polymer, water, and the like are blended in an adhesive layer which comes into direct contact with an applied site is caused to contain specific amounts of an alum and sodium edetate in combination, and also a composition to be mixed is mixed such that the temperature becomes a specific mixing temperature when the adhesive layer composition is obtained, in a cooling sheet including an adhesive layer formed by molding an adhesive layer composition obtained by the mixing, even when the content of the water (that is, water content) is as high as 69% by mass or more, occurrence of spread unevenness and seepage of the adhesive layer is sufficiently suppressed, and have consequently completed the present invention.

Specifically, the method for producing an adhesive layer composition for producing a cooling sheet of the present invention is a method for producing an adhesive layer composition for producing a cooling sheet including a backing layer, an adhesive layer, and a liner layer, the method comprising the step of:

mixing a composition to be mixed containing water, an alum, sodium edetate, a polyacrylic acid, and a neutralized polyacrylic acid such that a mixing temperature becomes 5 to 23° C., to obtain an adhesive layer composition, wherein in the composition to be mixed, a content of the water is 69 to 98.24% by mass relative to a total mass of the composition to be mixed, a content of the alum is 0.18 to 0.42% by mass relative to the total mass of the composition to be mixed, a content of the sodium edetate is 0.08 to 0.18% by mass relative to the total mass of the composition to be mixed, and a mass ratio between the content of the alum and the content of the sodium edetate (the content of the alum: the content of the sodium edetate) is 1:1 to 5.25:1.

As the method for producing an adhesive layer composition for producing a cooling sheet of the present invention, it is preferable that the composition to be mixed further contain a polyvinyl alcohol, and it is also preferable that the composition to be mixed further contain sodium carboxymethyl cellulose.

Moreover, as the method for producing an adhesive layer composition for producing a cooling sheet of the present invention, it is preferable that in the composition to be mixed, a content of the neutralized polyacrylic acid be 1 to 10% by mass relative to the total mass of the composition to be mixed.

The method for producing a cooling sheet of the present invention is a method for producing a cooling sheet including a backing layer, an adhesive layer, and a liner layer, the method comprising the steps of:

obtaining an adhesive layer composition by the method for producing an adhesive layer composition for producing a cooling sheet of the present invention; and molding the adhesive layer composition to obtain the adhesive layer, wherein the adhesive layer contains water, an alum, sodium edetate, a polyacrylic acid, and a neutralized polyacrylic acid, and in the adhesive layer, a content of the water is 69 to 98.24% by mass relative to a total mass of the adhesive layer, a content of the alum is 0.18 to 0.42% by mass relative to the total mass or the adhesive layer, a content of the sodium edetate is 0.08 to 0.18% by mass relative to the total mass of the adhesive layer, and a mass ratio between the content of the alum and the content of the sodium edetate (the content of the alum: the content of the sodium edetate) is 1:1 to 5.25:1.

As the method for producing a cooling sheet of the present invention, it is preferable that a mass of the adhesive layer be 1,500 to 2,300 g/m².

The cooling sheet of the present invention is a cooling sheet comprising a backing layer, an adhesive layer, and a liner layer, wherein the adhesive layer contains water, an alum, sodium edetate, a polyacrylic acid, and a neutralized polyacrylic acid, and in the adhesive layer, a content of the water is 69 to 98.24% by mass relative to a total mass of the adhesive layer, a content of the alum is 0.18 to 0.42% by mass relative to the total mass of the adhesive layer, a content of the sodium edetate is 0.08 to 0.18% by mass relative to the total mass of the adhesive layer, and a mass ratio between the content of the alum and the content of the sodium edetate (the content of the alum: the content of the sodium edetate) is 1:1 to 5.25:1, and a mixing temperature of an adhesive layer composition from which the adhesive layer is formed is 5 to 23° C.

As the cooling sheet of the present invention, it is preferable that the adhesive layer further contain a polyvinyl alcohol, and it is also preferable that the adhesive layer further contain sodium carboxymethyl cellulose.

Furthermore, as the cooling sheet of the present invention, it is preferable that a mass of the adhesive layer be 1,500 to 2,300 g/m².

The cooling sheet of the present invention is characterized in that the cooling sheet comprises an adhesive layer formed by molding an adhesive layer composition (formed by shaping the adhesive layer composition) obtained by the method for producing an adhesive layer composition for producing a cooling sheet of the present invention, and characterized in that a mixing temperature of the adhesive layer composition from which the adhesive layer is formed (from which the adhesive layer is shaped) is 5 to 23° C. The adhesive layer composition is obtained by mixing a composition to be mixed containing water, an alum, sodium edetate, a polyacrylic acid, and a neutralized polyacrylic acid in specific contents such that the temperature of the adhesive layer composition becomes a specific temperature. In the composition to be mixed, the alum functions mainly as a cross-linking agent, the sodium edetate functions mainly as a chelating agent. The present inventors surmise that in the present invention, by setting the composition and mixing temperature of the composition to be mixed within specific ranges, it becomes possible to set the degrees of the cross-linking and chelating by these functions within ranges that enable occurrence of spread unevenness and seepage of the obtained adhesive layer to be sufficiently suppressed. In such mixing, the alum and the sodium edetate work together in the water, the polyacrylic acid, and the neutralized polyacrylic acid such that the alum functions as a cross-linking agent and the sodium edetate functions as a chelating agent. Hence, the obtained adhesive layer composition and the structure of the adhesive layer formed by molding the adhesive layer composition are complicated and wide-ranging, so that it is significantly difficult to analyze the structure or the properties. Thus, in the cooling sheet of the present invention, there are impossible and impractical circumstances in terms of directly specifying the adhesive layer by means of the structure or the properties.

Advantageous Effects of Invention

The present invention makes it possible to provide a method for producing an adhesive layer composition that allows the production of a cooling sheet of a type in which a water-soluble polymer, water, and the like are blended in an adhesive layer which comes into direct contact with an applied site, the cooling sheet having a sufficiently high water content (for example, 65% by mass or more) and allowing occurrence of spread unevenness and seepage of the adhesive layer to be sufficiently suppressed, a method for producing a cooling sheet using the same, and a cooling sheet obtained by these.

DESCRIPTION OF EMBODIMENTS

Hereinafter, the present invention will be described in detail based on preferred embodiments thereof.

Method for Producing an Adhesive Layer Composition for Producing a Cooling Sheet The method for producing an adhesive layer composition for producing a cooling sheet of the present invention (hereinafter, sometimes referred to simply as a "method for producing an adhesive layer composition") is a method for producing an adhesive layer composition for producing a cooling sheet including a backing layer, an adhesive layer, and a liner layer, the method comprising the step of:
mixing a composition to be mixed containing water, an alum, sodium edetate, a polyacrylic acid, and a neutralized polyacrylic acid such that a mixing temperature becomes 5 to 23° C., to obtain an adhesive layer composition, wherein
in the composition to be mixed,
a content of the water is 69 to 98.24% by mass relative to a total mass of the composition to be mixed,
a content of the alum is 0.18 to 0.42% toy mass relative to the total mass of the composition to be mixed,
a content of the sodium edetate is 0.08 to 0.18% by mass relative to the total mass of the composition to be mixed, and
a mass ratio between the content of the alum and the content of the sodium edetate (the content of the alum: the content of the sodium edetate) is 1:1 to 5.25:1. It is possible to obtain an adhesive layer of the cooling sheet by molding the adhesive layer composition obtained by this production method.

Backing Layer

The backing layer according to the present invention only has to be capable of backing the adhesive layer, and includes, for example, a publicly-known backing layer for cooling sheets. The thickness of the backing layer is not particularly limited, but is preferably within a range of 5 to 1,500 μm, and more preferably within a range of 5 to 1,000 μm, from the viewpoint of easiness in work in applying the cooling sheet and easiness in production.

The form of the backing layer according to the present invention includes, for example, films; sheets such as a sheet, a sheet-shaped porous body, and a sheet-shaped foam; fabrics such as a woven fabric, a braided fabric, and a nonwoven fabric; foils; and laminates of these. Among these, a fabric is preferable from the viewpoint that a fabric is a form that can cause seepage of an adhesive layer because of its breathability and water permeability and thus requires more the effect to suppress occurrence of seepage achieved by the adhesive layer composition obtained by the production method of the present invention. From the same viewpoint, the basis weight of the fabric is preferably 90 g/m² or more, more preferably 90 to 200 g/m², further preferably 90 to 160 g/m², and even more preferably 90 to 110 g/m². If the basis weight is less than the lower limit, there is a tendency that shape breakage such as tearing, poor external appearance, difficulty in application during the application is caused, while if the basis weight is more than the upper limit, a decrease in usability due to poor stretchability and poor flexibility, turning during the application, and an increase in cost are caused.

The material of the backing layer according to the present invention is not particularly limited, and includes, for example, synthetic resins including polyolefins such as polyethylene and polypropylene ethylene-vinyl acetate copolymer, vinyl acetate-vinyl chloride copolymer, polyvinyl chloride, and the like; polyamides such as nylon; polyesters such as polyethylene terephthalate (PET), polybutylene terephthalate, and polyethylene naphthalate; cellulose derivatives; polyamides such as nylon; rayon; and polyurethane, metals such as aluminum, as well as rayon; pulp; and cotton.

Liner Layer

The liner layer of the present invention only has to be capable of protecting the adhesive layer until the usage, is not particularly limited, and includes, for example, a publicly-known liner layer (also referred to as a "release liner") for cooling sheets. The liner layer of the present invention includes, for example, films and sheets made of synthetic resins including polyolefins such as polyethylene and polypropylene; ethylene-vinyl acetate copolymer, vinyl acetate-vinyl chloride copolymer, polyvinyl chloride, and the like; polyamides such as nylon; polyesters such as polyethylene terephthalate; cellulose derivatives; and polyurethane, aluminum, paper, and the like, as well as laminates of these. Such a liner layer is preferably a liner layer subjected to release treatment such as silicone-containing compound coating or fluorine-containing compound coating on a surface thereof which comes into contact with the adhesive layer so that the liner layer can be easily peeled off the adhesive layer.

Composition to be Mixed

The composition to be mixed in the method for producing an adhesive layer composition of the present invention contains water, an alum, sodium edetate, a polyacrylic acid, and a neutralized polyacrylic acid.

Water

The water according to the present invention is not particularly limited, but water subjected to purification such as ion exchange, distillation, or filtration is preferable, and, for example, "purified water" described in Japanese Pharmacopoeia (Japanese Pharmacopoeia 17th Edition) can be favorably used.

It is necessary that the content of the water in the composition to be mixed according to the present invention be 69 to 98.24% by mass relative to the total mass of the composition to be mixed. If the content of the water is less than the lower limit, sufficiently excellent cooling power and cooling duration cannot be achieved in the obtained adhesive layer, so that the cooling performance becomes insufficient, while if the content of the water is more than the upper limit, seepage and so-called liner displacement in which the linear layer is displaced from the adhesive layer during the storage become likely to occur in the obtained adhesive layer, and also the adhesive force (adhesion) becomes insufficient. In addition, from the same viewpoint, the content of the water is more preferably 69 to 30% by mass, and further preferably 70 to 80% by mass, relative to the total mass of the composition to be mixed.

Alum

It is necessary that the composition to be mixed according to the present invention contain an alum. In the present invention, the "alum" collectively refers to double salts of a sulfate of monovalent cations and a sulfate of trivalent metal ions. The alum includes potassium alum, ammonium alum, and iron alum, and may be one of these alone or a mixture of two or more of these. Among these, potassium alum is preferable, and the potassium alum includes potassium aluminium sulfate. The potassium aluminium sulfate is normally generated by dissolving aluminum in potassium hydroxide and then adding sulfuric acid thereto, and is also referred to simply as alum and dried alum depending on the presence or absence of crystalline water.

It is necessary that the content of the alum in the composition to be mixed according to the present invention be 0.18 to 0.42% by mass relative to the total mass of the composition to be mixed. If the content of the alum is less than the lower limit, seepage becomes likely to occur in the obtained adhesive layer, while if the content of the alum is more than the upper limit, spread unevenness occurs in the adhesive layer or it becomes difficult to obtain sufficient adhesive force. In addition, from the same viewpoint, the content of the alum is more preferably 0.2 to 0.4% by mass relative to the total mass of the composition to be mixed.

Sodium Edetate

It is necessary that the composition to be mixed according to the present invention contain sodium edetate. Sodium edetate is also referred to as ethylenediaminetetraacetic acid disodium salt and sodium EDTA. It is necessary that the content of the sodium edetate in the composition to be mixed according to the present invention be 0.08 to 0.18% by mass relative to the total mass of the composition to be mixed. If the content of the sodium edetate is less than the lower limit, spread unevenness becomes likely to occur in the obtained adhesive layer or it becomes difficult to obtain sufficient adhesive force, while if the content of the sodium edetate is more than the upper limit, seepage becomes likely to occur in the obtained adhesive layer. In addition, from the same viewpoint, the content of the sodium edetate is more preferably 0.1 to 0.17% by mass relative to the total mass of the composition to be mixed.

In addition, in the composition to be mixed according to the present invention, it is necessary that a mass ratio between the content of the alum and the content of the sodium edetate (the content of the alum: the content of the sodium edetate) be 1:1 to 5.25:1. If the ratio of the content of the alum to the content of the sodium edetate is less than the lower limit, seepage becomes likely to occur in the obtained adhesive layer, while it the ratio of the content of the alum to the content of the sodium edetate is more than the upper limit, spread unevenness occurs in the obtained adhesive layer or it becomes difficult to obtain sufficient adhesive force. In addition, from the same viewpoint, the mass ratio between the content of the alum and the content of the sodium edetate (the content of the alum: the content of the sodium edetate) is more preferably 1:1 to 3:1, and further preferably 1.33:2 to 2.67:1.

Water-Soluble Polymer

The composition to be mixed according to the present invention contains a polyacrylic acid as a first water-soluble polymer. The content of the polyacrylic acid in the composition to be mixed according to the present invention is preferably 0.5 to 5% by mass, and more preferably 1 to 3% by mass, relative to the total mass of the composition to be mixed. If the content of the polyacrylic acid is less than the lower limit, there is a tendency that the hardness of the obtained adhesive layer becomes high, so that it becomes difficult to obtain sufficient adhesive force, and liner displacement becomes likely to occur, while if the content of the polyacrylic acid is more than the upper limit, there is a tendency that the effect to suppress liner displacement and the effect to suppress occurrence of seepage owing to the maintenance of the moldability and shape retention of the obtained adhesive layer decrease.

The composition to be mixed according to the present invention contains a neutralized polyacrylic acid as a second water-soluble polymer. By further blending the neutralized polyacrylic acid as a water-soluble polymer, the moldability and shape retention of the obtained adhesive layer is made higher. In the present invention, the "neutralized polyacrylic acid" includes "partially neutralized polyacrylic acid", and the neutralized polyacrylic acid according to the present invention refers to what is obtained by neutralizing all or some of carboxy groups of polyacrylic acid with an alkali metal such as sodium or potassium, ammonium ions, or the like. The neutralized polyacrylic acid includes, for example, sodium polyacrylate, potassium polyacrylate, ammonium polyacrylate, and the like, and may be one of these alone or a mixture of two or more of these. Among these, sodium polyacrylate is preferable from the viewpoint that the moldability and shape retention of the obtained adhesive layer tends to become even higher. The neutralization rate of the neutralized polyacrylic acid is not particularly limited, but is preferably 30 to 100%, for example.

The content of the neutralized polyacrylic acid in the composition to be mixed according to the present invention is preferably 1 to 10% by mass, and more preferably 3 to 7.5% by mass, relative to the total mass of the composition to be mixed. If the content of the neutralized polyacrylic acid is less than the lower limit, there is a tendency that the effects to suppress spread unevenness and seepage decrease in the obtained adhesive layer, while if the content of the neutralized polyacrylic acid is more than the upper limit, there is a tendency that a decrease in the effect to suppress occurrence of spread unevenness and a decrease in the adhesive force of the adhesive layer become more likely to occur in the obtained adhesive layer.

In addition, in the composition to be mixed according to the present invention, a total content of the polyacrylic acid and the neutralized polyacrylic acid is preferably 1.5 to 15% by mass, and more preferably 4 to 10.5% by mass, relative to the total mass of the composition to be mixed. If the total content is less than the lower limit, there is a tendency that the effect to suppress occurrence of seepage decreases in the obtained adhesive layer, while if the total content is more than the upper limit, there is a tendency that the hardness of the obtained adhesive layer becomes high, so that it becomes difficult to obtain sufficient adhesive force and spread unevenness becomes like to occur in the adhesive layer.

It is preferable that the composition to be mixed according to the present invention further contain a polyvinyl alcohol as a third water-soluble polymer. When a polyvinyl alcohol is further combined as a water-soluble polymer, there is a tendency that it becomes possible to maintain the adhesive force at a more sufficiently high level while more sufficiently suppressing occurrence of spread unevenness and seepage even in a case where the mass of the obtained adhesive layer is increased (for example, increased to 1,500 g/m$^2$ or more).

In the case where the composition to be mixed according to the present invention further contains the polyvinyl alcohol, the content of the polyvinyl alcohol is preferably 3 to 10% by mass, and more preferably 4 to 6% by mass, relative to the total mass of the composition to be mixed. If the content of the polyvinyl alcohol is less than the lower limit, there is a tendency that the effect to suppress liner displacement and the effect to suppress occurrence of seepage due to the maintenance of the moldability and shape retention of the obtained adhesive layer decrease, while if the content of the polyvinyl alcohol is more than the upper limit, there is a tendency that the hardness of the obtained adhesive layer becomes high, so that more sufficient adhesive force cannot be obtained.

In addition, in the case where the composition to be mixed according to the present invention contains the polyvinyl alcohol, a mass ratio between the content of the polyvinyl alcohol and the content of the polyacrylic acid (the content of the polyvinyl alcohol: the content of the polyacrylic acid) is preferably 1.2:1 to 5:1, more preferably 1.3:1 to 4:1, and further preferably 1.5:1 to 3:1. When the ratio of the content of the polyvinyl alcohol to the content of the polyacrylic acid is within the above range, there is a tendency that the moldability and shape retention and the adhesive force of the obtained adhesive layer becomes more favorable, and the liner displacement is also suppressed more.

It is preferable that the composition to be mixed according to the present invention further contain sodium carboxymethyl cellulose (also referred to as "carmellose sodium") as a fourth water-soluble polymer. When sodium carboxymethyl cellulose is further combined as a water-soluble polymer, there is a tendency that the moldability and shape retention of the obtained adhesive layer become further favorable.

In the case where the composition to be mixed according to the present invention further contains the sodium carboxymethyl cellulose, the content of the sodium carboxymethyl cellulose is preferably 0.5 to 5% by mass, and more preferably 0.5 to 3% by mass, relative to the total mass of the composition to be mixed. If the content of the sodium carboxymethyl cellulose is less than the lower limit, there is a tendency that the effect to suppress occurrence of seepage in the obtained adhesive layer decreases, while if the content of the sodium carboxymethyl cellulose is more than the upper limit, there is a tendency that spread unevenness becomes likely to occur in the obtained adhesive layer.

The composition to be mixed according to the present invention may further contain a water-soluble polymer other than the first to fourth water-soluble polymers as long as the advantageous effects of the present invention are not impaired. Such other water-soluble polymer includes, for example, gelatin, polyvinylpyrrolidone, sodium alginate, hydroxypropyl cellulose, methyl cellulose, carrageenan, glucomannan, agar, guar gum, xanthan gum, gellan gum, pectin, locust bean gum, and may be one of these alone or a mixture of two or more of these. In the case where the composition to be mixed according to the present invention further contains the other water-soluble polymer, the content of the other water-soluble polymer is preferably 5% by mass or less relative to the total mass of the composition to be mixed.

Other Components

The composition to be mixed according to the present invention may further contain other components other than the above components as long as the advantageous effects of the present invention are not impaired. Such other components include, for example, a surfactant, an antiseptic, a refreshing agent, a humectant (moisturizer), a filler (excipient), a colorant, an organic acid (for example, tartaric acid), and may be one of these alone or a mixture of two or more of these.

The surfactant includes, for example, polyalkylene glycol monooleate, polyethylene glycol monostearate, and polyoxyethylene sorbitan monooleate, and may be one of these alone or a mixture of two or more of these. Among these, polyalkylene glycol monooleate is preferable from the viewpoint that there is a tendency that the adhesive force becomes more favorable while occurrence of liner displacement and seepage are more sufficiently suppressed in the obtained adhesive layer.

Such polyalkylene glycol monooleate includes, for example, polyethylene glycol monooleate, polypropylene glycol monooleate, polyethylene-polypropylene glycol monooleate, and the like, and among these, polyethylene glycol monooleate is preferable.

In the case where the composition to be mixed according to the present invention further contain the surfactant, the content of the surfactant is preferably 0.12 to 0.7% by mass, more preferably 0.15 to 0.5% by mass, and further preferably 0.2 to 0.4% by mass, relative to the total mass of the composition to be mixed. If the content of the surfactant is less than the lower limit, in the case where an antiseptic described below (particularly, a parahydroxybenzoate) is contained in the adhesive layer, which has a high water content, for example, there is a tendency that it becomes difficult to completely dissolve the antiseptic, so that the effect to prevent generation of bacteria and fungi cannot be sufficiently exerted, while if the content of the surfactant is more than the upper limit, there is a tendency that the effect to suppress liner displacement and the effect to suppress occurrence of seepage due to the maintenance of the moldability and shape retention of the obtained adhesive layer decrease.

The antiseptic is not particularly limited, includes, for example, parahydroxybenzoates, isopropyl methylphenols, and the like, and may be one of these alone or a mixture of two or more of these. Among these, parahydroxybenzoates are preferable from the viewpoint that there is a tendency that parahydroxybenzoate is capable of preventing generation of bacteria and fungi in the obtained adhesive layer over a longer period of time.

Such parahydroxybenzoates include, for example, methyl parahydroxybenzoate (methylparaben), ethyl parahydroxybenzoate (ethylparaben), propyl parahydroxybenzoate (propylparaben), isopropyl parahydroxybenzoate (isopropylparaben), butyl parahydroxybenzoate (butylparaben), isobutyl parahydroxybenzoate (isobutylparaben), and the like, and among these, methyl parahydroxybenzoate, ethyl parahydroxybenzoate, and propyl parahydroxybenzoate are preferable.

In the case where the composition to be mixed according to the present invention further contains the antiseptic, the content of the antiseptic is preferably 0.01 to 1% by mass, more preferably 0.05 to 0.5% by mass, and further preferably 0.05 to 0.3% by mass, relative to the total mass of the composition to be mixed. If the content of the antiseptic is less than the lower limit, there is a tendency that the effect to prevent generation of bacteria and fungi in the obtained adhesive layer cannot be sufficiently exerted, while if the content of the antiseptic is more than the upper limit, there is a tendency that part of the antiseptic is not dissolved and remains as a solid component in the adhesive layer, lowering the uniformity of the adhesive layer and impairing the external appearance.

The refreshing agent is for further improving the cooling performance such as cooling power and cooling duration when the cooling sheet is used, and may have an aroma. Such a refreshing agent includes, for example, thymol, l-menthol, dl-menthol, 1-isopulegol, Japanese mint oil, and the like, and may be one of these alone or a mixture of two or more of these. In the case where the composition to be mixed according to the present invention further contains the refreshing agent, the content of the refreshing agent is preferably 0.01 to 1% by mass, and more preferably 0.03 to 0.5% by mass, relative to the total mass of the composition to be mixed. If the content of the refreshing agent is less than the lower limit, there is a tendency that it is difficult to obtain a sufficient refreshing sensation, while if the content of the refreshing agent is more than the upper limit, there is a tendency that the refreshing sensation becomes too strong.

The humectant (moisturizer) includes, for example, polyhydric alcohols such as glycerin, propylene glycol, 1,3-butylene glycol, and sorbitol, and may be one of these alone or a mixture of two or more of these. In the case where the composition to be mixed according to the present invention further contains the humectant, the content of the humectant is preferably 10 to 60% by mass relative to the total mass of the composition to be mixed. If the content of the humectant is less than the lower limit, there is a tendency chat it becomes difficult to obtain a sufficient moisturizing effect, while if the content of the humectant is more than the upper limit, there is a tendency that the solubility of the water-soluble polymer becomes likely to decrease.

The filler (excipient) includes, for example, inorganic substances such as kaolin, zinc oxide, titanium oxide, talc, bentonite, hydrous aluminum silicate, and magnesium aluminometasilicate, and may be one of these alone or a mixture of two or more of these. In the case where the composition to be mixed according to the present invention further contain the filler, the content of the filler is preferably 6% by mass or lees relative to the total mass of the composition to be mixed. If the content of the filler is more than the upper limit, there is a tendency that the adhesive force of the adhesive layer is likely to decrease.

Mixing

In the method for producing an adhesive layer composition of the present invention, the composition to be mixed is mixed such that a mixing temperature becomes 5 to 23° C., to obtain an adhesive layer composition.

In the present invention, the "mixing temperature" is more specifically a temperature corresponding to the temperature of the composition at the completion of the mixing, indicates the temperature of the composition at the completion of the mixing, and can be checked by measuring the temperature of the composition to be mixed (that is, the adhesive layer composition) at the completion of the mixing using a thermometer. The completion of the mixing is preferably within 5 minutes from when the composition to be mixed is completely stopped. It is necessary that, the mixing temperature according to the present invention be 5 to 23° C. If the mixing temperature is less than the lower limit, seepage becomes likely to occur in the obtained adhesive layer, while if the mixing temperature is more than the upper limit, spread unevenness becomes likely to occur in the obtained adhesive layer. In addition, from the same viewpoint, the mixing temperature is more preferably 6 to 23° C., and more preferably 7 to 23° C.

The mixing method includes, for example, a method that places the composition to be mixed in a container and mixes the composition to be mixed using a mixer such as a propeller mixer, a paddle mixer, an anchor mixer, a planetary mixer, a V mixer, a Henschel mixer, or the like.

Since the temperature of the composition to be mixed tends to be increased by such mixing, in the mixing according to the present invention, the temperature of the composition to be mixed may exceed the mixing temperature from the start of the mixing to the completion of the mixing, but the temperature of the composition to be mixed preferably does not exceed 25° C., is preferably maintained at 25° C. or less, and is more preferably maintained at 5 to 25° C., from the start of the mixing to the completion of the mixing. In addition, since the temperature of the composition to be mixed tends to be increased by the mixing as such, in the present invention, it is preferable to mix the composition to be mixed while cooling the composition to be mixed. Such cooling conditions can be adjusted as appropriate depending on the composition and amount of the composition to be mixed.

The time for the mixing (mixing time: time from the start of the mixing to the completion of the mixing) only has to be such that the composition to be mixed becomes uniform, and can be adjusted as appropriate depending on the composition and amount of the composition to be mixed and is not particularly limited, but for example, is preferably 5 to 60 minutes, and more preferably 5 to 30 minutes. When the mixing time is within the above range, there is a tendency that the composition to be mixed becomes sufficiently uniform, and it is possible to obtain an adhesive layer composition that satisfies the condition of the mixing temperature at the completion of the mixing.

Since it is possible to obtain an adhesive layer which has a high water content and in which occurrence of spread unevenness and seepage is sufficiently suppressed, by molding an adhesive layer composition obtained by the method for producing an adhesive layer composition of the present invention, the adhesive layer composition can be used favorably in production of a cooling sheet including the adhesive layer.

Cooling Sheet and Method for Production the Same

The method for producing a cooling sheet of the present invention is a method for obtaining a cooling sheet by using an adhesive layer composition obtained by the method for producing an adhesive layer composition of the present invention, and comprises the steps of:
    obtaining an adhesive layer composition by the method for producing an adhesive layer composition of the present invention; and molding the adhesive layer composition to obtain the adhesive layer, wherein the adhesive layer contains water, an alum, sodium edetate, a polyacrylic acid, and a neutralized polyacrylic acid, and in the adhesive layer, a content of the water is 69 to 98.24% by mass relative to a total mass of the adhesive layer, a content of the alum is 0.18 to 0.42% by mass relative to the total mass of the adhesive layer, a content, of the sodium edetate is 0.08 to 0.18% by mass relative to the total mass of the adhesive layer, and a mass ratio between the content of the alum and the content of the sodium edetate (the content of the alum: the content of the sodium edetate) is 1:1 to 5.25:1.

Furthermore, the cooling sheet of the present, invention is the cooling sheet which includes the backing layer, the adhesive layer, and the liner layer, and which is obtained by the method for producing a cooling sheet of the present invention, wherein a mixing temperature of an adhesive layer composition, from which the adhesive layer is formed is 5 to 23° C.

In the cooling sheet and the method for producing the same of the present invention, the composition of the adhesive layer is the same as a composition obtained by replacing the "composition to be mixed" in the above-described composition of the composition to be mixed with the "adhesive layer", including the preferable embodiments. In addition, the backing layer and the liner layer are as described above. Furthermore, in the cooling sheet of the present invention, the mixing temperature of the adhesive layer composition from which the adhesive layer is formed is the same as the mixing temperature in the method for producing an adhesive layer composition of the present invention, including the preferable embodiments.

As the method for producing a cooling sheet of the present invention, for example, as a first embodiment, the cooling sheet, of the present invention can be obtained by: first obtaining an adhesive layer composition by the above method for producing an adhesive layer composition of the present invention; then molding the adhesive layer composition thus obtained by spreading the adhesive layer composition on one surface of the backing layer so as to have a desired mass per unit area to form the adhesive layer; subsequently, laminating the liner layer to a surface of the adhesive layer opposite to the backing layer; and cutting the laminate into a desired shape as necessary. The spreading method includes, for example, a direct coating method that spreads the adhesive layer composition on the backing layer by using a knife coater, a roll coater, a die coater, or the like, and the like.

In addition, as a second embodiment, the cooling sheet of the present invention can be obtained by: first obtaining an adhesive layer composition by the above method for producing an adhesive layer composition of the present invention; then molding the adhesive layer composition thus obtained by spreading the adhesive layer composition on one surface of the liner layer so as to have a desired mass per unit area by the same method as the method given above to form the adhesive layer; subsequently laminating the backing layer to a surface of the adhesive layer opposite to the liner layer; and cutting the laminate into a desired shape as necessary.

Since the mixing temperature (that is, the temperature of the composition to be mixed at the completion of the mixing), that is, the temperature of the adhesive layer composition immediately after the production is 5 to 23° C., the adhesive layer composition obtained by the method for producing an adhesive layer composition of the present invention is preferably molded before the temperature increases, and the temperature of the adhesive layer composition preferably does not exceed 23° C., and is preferably maintained at 23° C. or less until the adhesive layer is formed, depending on the environment for producing the cooling sheet. In addition, in the method for producing a cooling sheet of the present invention, after the adhesive layer composition is molded, the molded adhesive layer composition may be left to stand until the adhesive layer is stabilized.

In the cooling sheer, of the present invention, the mass of the adhesive layer (the mass per unit area of the applying surface) is not particularly limited, but is preferably 500 $g/m^2$ or more, more preferably 750 $g/m^2$ or more, further preferably 1,000 $g/m^2$ or more, and particularly preferably 1,500 $g/m^2$ or more, because there is a tendency that occurrence of seepage is sufficiently suppressed even in the case where the content of the water in the adhesive layer is increased and further the mass of the adhesive layer is increased in the cooling sheet of the present invention. If the mass of the adhesive layer is less than the lower limit, there is a tendency that it becomes difficult to obtain sufficient cooling performance such as cooling power and cooling duration. On the other hand, the upper limit for the mass of the adhesive layer is preferably 2,300 $g/m^2$. If the mass of the adhesive layer is more than the upper limit, seepage becomes likely to occur even in the cooling sheet of the present invention in some cases.

In addition, in the cooling sheet of the present invention, the area of the applying surface of the adhesive layer is not particularly limited, but is preferably 10 to 300 $cm^2$, more preferably 20 to 150 $cm^2$, and further preferably 30 to 70 $cm^2$. If the area of the applying surface is less than the lower limit, there is a tendency that it becomes difficult to obtain a sufficient cooling effect, while if the area of the applying surface is more than the upper limit, the adhesion decreases, so that the cooling sheet becomes likely to be peeled off.

In addition, the cooling sheer, of the present invention may be enclosed in a packaging container for storage (for example, an aluminum packaging bag) as a packaged formulation as necessary.

Examples

Hereinafter, the present invention will be described in further detail based on Examples and Comparative Examples, but the present invention is not limited to Examples described below. Note that various tests in Examples and Comparative Examples were conducted in accordance with methods described below.

(1) Test for Measuring Mixing Temperature

In each of Examples and Comparative Examples, the temperature of the composition to be mixed immediately after mixing (within 5 minutes after the mixer was stopped) (the temperature of the adhesive layer composition) was measured using a thermometer (a temperature sensor for semisolid substances and liquids in general, manufactured by Anritsu Meter Co., Ltd., AP-400K) as the mixing temperature (° C.).

(2) Test for Checking Spread Unevenness of Adhesive Layer

The liner layer of the cooling sheet obtained in each of Examples and Comparative Examples was peeled off and the property (uniformity) of the adhesive layer was visually checked and evaluated in compliance with the following evaluation scores:
- 0: The surface and the thickness were uniform with no spread unevenness in the entire surface (area: 95% or more) of the adhesive layer.
- 1: The surface and/or the thickness was not uniform in part (area: more than 5% and less than 50%) of the adhesive layer and spread unevenness was observed.
- 2: The surface and/or the thickness was not uniform in large part of or the entire surface (area: 50% or more) of the adhesive layer and spread unevenness was observed. The evaluation was conducted on three cooling sheets for each in the same manner and the average value of the scores was used as an evaluation result, and the cooling sheet whose score (average value) was 0 was determined to be allowable.

(3) Test for Checking Seepage of Adhesive Layer

The cooling sheet obtained in each of Examples and Comparative Examples was enclosed in an aluminum packaging bag and was left to stand at room temperature for 24 hours or more, and thereafter the packaging bag was opened, and the area of a portion where the adhesive layer was seeped into the backing layer was measured and was evaluated in compliance with the following evaluation scores:
- 0: There was no seepage.
- 1: There was a small amount of seepage (area: less than 10%).
- 2: There was some seepage (area: 10% or more and less than 20%).
- 3: There was an amount of seepage (area: 20% or more and less than 30%).
- 4: There was a considerable amount of seepage (area: 30% or more). The evaluation was conducted on three cooling sheets for each in the same manner and the average value of the scores was used as an evaluation result, and the cooling sheet whose score (average value) was 0 was determined to be allowable.

(4) Test for Checking Cooling Performance

The cooling sheet obtained in each of Examples and Comparative Examples was enclosed in an aluminum packaging bag and was left to stand at room temperature for 2 weeks or more, and thereafter the packaging bag was opened and the cooling duration of the cooling sheet was measured in accordance with the following procedures and evaluated in compliance with the following evaluation scores. The cooling sheet whose score was 1 or less was determined to be allowable.

Measurement Procedures (i) Water is placed in a constant temperature oven and the temperature of the water is set at 34° C.
(ii) A data logger equipped with a temperature sensor is fixed on an outer surface of the constant temperature oven by using an adhesive tape. At this time, it is made sure that the adhesive tape does not touch the temperature sensor.
(iii) Recording of the temperature from the data logger is started. Data is acquired every 5 minutes.
(iv) The liner layer of the cooling sheet is peeled off, and the surface of the cooling sheet on the adhesive layer side is applied onto the temperature sensor to cover the temperature sensor with the cooling sheet.
(v) After the temperature sensor is covered with the cooling sheet, the recording of the temperature is continued for 12 hours or more.
(vi) Starting from the time when the temperature starts decreasing, the time until when the decreased temperature starts increasing again is defined and measured as the cooling duration.

Evaluation Scores

- 0: Excellent (cooling duration: 5 hours or more)
- 1: Good (cooling duration: 3 hours or more and less than 5 hours)
- 2: Slightly bad (cooling duration: 1 hour or more and less than 3 hours)
- 3: Bad (cooling duration: less than 1 hour).

Example 1

First, 4.00 parts by mass of polyvinyl alcohol, 1.92 parts by mass of a polyacrylic acid, 4.58 parts by mass of a partially neutralized sodium polyacrylate, 15.00 parts by mass of concentrated glycerin, 1.00 parts by mass of sodium carboxymethyl cellulose, 0.24 parts by mass of potassium aluminium sulfate, 0.15 parts by mass of sodium edetate, 0.30 parts by mass of polyethylene glycol monooleate (the average number of moles of ethyleneoxy groups added; 6 (6EO)), 72.3775 parts by mass of purified water, and 0.4325 parts by mass of the other components (tartaric acid, 1-menthol, methyl parahydroxybenzoate, propyl parahydroxybenzoate, and Blue No. 1), were weighed to obtain a composition to be mixed. The composition to be mixed was mixed so as to be uniform by using a mixer while the composition to be mixed was cooled such that the mixing temperature became 23° C. or less, to obtain an adhesive layer composition having a composition described in Table 1. The adhesive layer composition thus obtained was spread on a surface of a liner layer (release-treated polyester film) such that the mass per unit area became 1,900 g/m$^2$ to form an adhesive layer, and then, a backing layer (polyethylene terephthalate nonwoven fabric, basis weight: 100 g/m$^2$) was applied onto a surface of the adhesive layer opposite to the liner layer, followed by cutting into a size of 5 cm×11 cm to obtain a cooling sheet.

Comparative Examples 1 to 3

Each cooling sheet was obtained in the same manner as in Example 1 except that magnesium aluminometasilicate (Comparative Example 1), dihydroxyaluminum aminoacetate (Comparative Example 2), or aluminum silicate (Comparative Example 3) was used as a cross-linking agent instead of potassium aluminium sulfate.

In each of Example 1 and Comparative Examples 1 to 3, the test (1) was conducted on the obtained adhesive layer composition, and the tests (2) to (4) were conducted on the obtained cooling sheet. The composition of each composition to be mixed (that is, the composition of the adhesive layer composition, the composition of the adhesive layer) as well as results of the respective tests (1) to (3) are shown in Table 1 given below. In the following tables, A:B represents the mass ratio between (A) the component of the cross-linking agent and (B) the sodium edetate in the table. Note that in Example 1, the evaluation result of the test (4) was 0 and was surely allowable.

TABLE 1

|  | Example 1 | Comparative Example 1 | Comparative Example 2 | Comparative Example 3 |
|---|---|---|---|---|
| Polyvinyl alcohol | 4.00 | 4.00 | 4.00 | 4.00 |
| Polyacrylic acid | 1.92 | 1.92 | 1.92 | 1.92 |
| Partially neutralized sodium polyacrylate | 4.58 | 4.58 | 4.58 | 4.58 |
| Concentrated glycerin | 15.00 | 15.00 | 15.00 | 15.00 |
| Sodium carboxymethyl cellulose | 1.00 | 1.00 | 1.00 | 1.00 |
| (A) Potassium aluminium sulfate | 0.24 | — | — | — |
| Magnesium aluminometasilicate | — | 0.24 | — | — |
| Dihydroxyaluminum aminoacetate | — | — | 0.24 | — |
| Aluminum silicate | — | — | — | 0.24 |
| (B) Sodium edetate | 0.15 | 0.15 | 0.15 | 0.15 |
| Polyethylene glycol monooleate (6EO) | 0.30 | 0.30 | 0.30 | 0.30 |
| Purified water | 72.3775 | 72.3775 | 72.3775 | 72.3775 |
| Others | 0.4325 | 0.4325 | 0.4325 | 0.4325 |
| Total [parts by mass] | 100 | 100 | 100 | 100 |
| A:B [mass ratio] | 1.6:1 | 1.6:1 | 1.6:1 | 1.6:1 |
| Mixing temperature [° C.] | 12.7 | 12.6 | 12.7 | 12.6 |
| Spread unevenness of the adhesive layer | 0 | 0 | 0 | 0 |
| Seepage of the adhesive layer | 0 | 1 | 2 | 4 |

As shown in Table 1, in the cooling sheet (for example, Example 1) of the present invention obtained by molding the adhesive layer composition obtained with specific composition and conditions using potassium aluminium sulfate, it was confirmed that even though the water content was 69% by mass or more, which was sufficiently high, an excellent cooling effect was exerted, occurrence of spread unevenness of the adhesive layer was sufficiently suppressed, and occurrence of seepage of the adhesive layer into the backing layer was also sufficiently suppressed over a long period of time. On the other hand, in the cooling sheets (Comparative Examples 1 to 3) obtained by using cross-linking agents other than potassium aluminium sulfate, it was confirmed that particularly, seepage of the adhesive layer into the backing layer was likely to occur.

Examples 2 to 8 and Comparative Examples 4 to 7

Each cooling sheet was obtained in the same manner as in Example 1 except that the contents of potassium aluminium sulfate and sodium edetate were changed, and the composition of each composition to be mixed was changed to the composition shown in Table 2 to Table 3 given below.

In each of Examples 2 to 8 and Comparative Examples 4 to 7, the test (1) was conducted on the obtained adhesive layer composition, and the tests (2) to (3) were conducted on the obtained cooling sheet. The composition of each composition no be mixed (than is, the composition of the adhesive layer composition, the composition of the adhesive layer) as well as the results of the respective tests (1) to (3) are shown in Tables 2 to 3 given below. In addition, the values of Example 1 is also shown together in Tables 2 to 3.

TABLE 2

|  | Comparative Example 4 | Example 2 | Example 1 | Example 3 | Example 4 | Example 5 | Comparative Example 5 |
|---|---|---|---|---|---|---|---|
| Polyvinyl alcohol | 4.00 | 4.00 | 4.00 | 4.00 | 4.00 | 4.00 | 4.00 |
| Polyacrylic acid | 1.92 | 1.92 | 1.92 | 1.92 | 1.92 | 1.92 | 1.92 |
| Partially neutralized sodium polyacrylate | 4.58 | 4.58 | 4.58 | 4.58 | 4.58 | 4.58 | 4.58 |
| Concentrated glycerin | 15.00 | 15.00 | 15.00 | 15.00 | 15.00 | 15.00 | 15.00 |
| Sodium carboxymethyl cellulose | 1.00 | 1.00 | 1.00 | 1.00 | 1.00 | 1.00 | 1.00 |
| (A) Potassium aluminium sulfate | 0.15 | 0.20 | 0.24 | 0.30 | 0.35 | 0.40 | 0.45 |
| (B) Sodium edetate | 0.15 | 0.15 | 0.15 | 0.15 | 0.15 | 0.15 | 0.15 |
| Polyethylene glycol monooleate (6EO) | 0.30 | 0.30 | 0.30 | 0.30 | 0.30 | 0.30 | 0.30 |
| Purified water | 72.4675 | 72.4175 | 72.3775 | 72.3175 | 72.2675 | 72.2175 | 72.1675 |
| Others | 0.4325 | 0.4325 | 0.4325 | 0.4325 | 0.4325 | 0.4325 | 0.4325 |
| Total [parts by mass] | 100 | 100 | 100 | 100 | 100 | 100 | 100 |
| A:B [mass ratio] | 1:1 | 4:3 | 1.6:1 | 2:1 | 7:3 | 8:3 | 3:1 |
| Mixing temperature [° C.] | 12.6 | 12.9 | 12.7 | 12.9 | 13.3 | 13.2 | 12.9 |
| Spread unevenness of the adhesive layer | 0 | 0 | 0 | 0 | 0 | 0 | 1 |
| Seepage of the adhesive layer | 2 | 0 | 0 | 0 | 0 | 0 | 0 |

TABLE 3

|  | Comparative Example 6 | Example 6 | Example 1 | Example 7 | Example 8 | Comparative Example 7 |
|---|---|---|---|---|---|---|
| Polyvinyl alcohol | 4.00 | 4.00 | 4.00 | 4.00 | 4.00 | 4.00 |
| Polyacrylic acid | 1.92 | 1.92 | 1.92 | 1.92 | 1.92 | 1.92 |
| Partially neutralized sodium polyacrylate | 4.58 | 4.58 | 4.58 | 4.58 | 4.58 | 4.58 |
| Concentrated glycerin | 15.00 | 15.00 | 15.00 | 15.00 | 15.00 | 15.00 |
| Sodium carboxymethyl cellulose | 1.00 | 1.00 | 1.00 | 1.00 | 1.00 | 1.00 |
| (A) Potassium aluminium sulfate | 0.24 | 0.24 | 0.24 | 0.24 | 0.24 | 0.24 |
| (B) Sodium edetate | 0.05 | 0.10 | 0.15 | 0.16 | 0.17 | 0.20 |
| Polyethylene glycol monooleate (6EO) | 0.30 | 0.30 | 0.30 | 0.30 | 0.30 | 0.30 |
| Purified water | 72.4775 | 72.4275 | 72.3775 | 72.3675 | 72.3575 | 72.3275 |
| Others | 0.4325 | 0.4325 | 0.4325 | 0.4325 | 0.4325 | 0.4325 |
| Total [parts by mass] | 100 | 100 | 100 | 100 | 100 | 100 |
| A:B [mass ratio] | 4.8:1 | 2.4:1 | 1.6:1 | 1.5:1 | 2.4:1.7 | 1.2:1 |
| Mixing temperature [° C.] | 13.1 | 13.6 | 12.7 | 12.5 | 13.2 | 13.2 |
| Spread unevenness of the adhesive layer | 1 | 0 | 0 | 0 | 0 | 0 |
| Seepage of the adhesive layer | 0 | 0 | 0 | 0 | 0 | 2 |

As shown in Tables 2 to 3, in the cooling sheets (for example, Examples 1, 2 to 8) of the present invention obtained by molding the adhesive layer compositions obtained with specific compositions and conditions, it was confirmed that even though the water content was 69% by mass or more, which was sufficiently high, occurrence of spread unevenness of the adhesive layer was sufficiently suppressed, and occurrence of seepage of the adhesive layer into the backing layer was also suppressed over a long period of time. On the other hand, in the cooling sheets (Comparative Examples 4 to 7) obtained by molding adhesive layer compositions whose compositions were out of the ranges of the specific composition according to the present invention, it was confirmed that the evaluation result of at least one of the spread unevenness of the adhesive layer and seepage of the adhesive layer into the backing layer was not sufficient.

Examples 9 to 12 and Comparative Examples 9 to 11

Each cooling sheet was obtained in the same manner as in Example 1 except that the composition of each composition to be mixed and the mixing temperature were changed respectively to the composition and temperature shown in Table 4 given below.

In each of Examples 9 to 12 and Comparative Examples 8 to 11, the test (1) was conducted on the adhesive layer composition, and the tests (2) to (3) were conducted on the cooling sheet. The composition of each composition to be mixed (the composition of the adhesive layer composition, the composition of the adhesive layer) as well as the results of the respective tests (1) to (3) are shown in Table 4 given below. In addition, the values of Examples 1, 3 to 5 are also shown together in Table 4.

TABLE 4

|  | Comparative Ex. 8 | Ex. 9 | Ex. 10 | Ex. 1 | Ex. 11 | Comparative Ex. 9 | Ex. 12 | Ex. 3 | Comparative Ex. 10 | Ex. 4 | Comparative Ex. 11 | Ex. 5 |
|---|---|---|---|---|---|---|---|---|---|---|---|---|
| Polyvinyl alcohol |  |  |  | 4.00 |  |  | 4.00 |  | 4.00 |  | 4.00 |  |
| Polyacrylic acid |  |  |  | 1.92 |  |  | 1.92 |  | 1.92 |  | 1.92 |  |
| Partially neutralized sodium polyacrylate |  |  |  | 4.58 |  |  | 4.58 |  | 4.58 |  | 4.58 |  |
| Concentrated glycerin |  |  |  | 15.00 |  |  | 15.00 |  | 15.00 |  | 15.00 |  |
| Sodium carboxymethyl cellulose |  |  |  | 1.00 |  |  | 1.00 |  | 1.00 |  | 1.00 |  |
| (A) Potassium aluminium sulfate |  |  |  | 0.24 |  |  | 0.30 |  | 0.35 |  | 0.40 |  |
| (B) Sodium edetate |  |  |  | 0.15 |  |  | 0.15 |  | 0.15 |  | 0.15 |  |
| Polyethylene glycol monooleate (6EO) |  |  |  | 0.30 |  |  | 0.30 |  | 0.30 |  | 0.30 |  |

TABLE 4-continued

| | Comparative Ex. 8 | Ex. 9 | Ex. 10 | Ex. 1 | Ex. 11 | Comparative Ex. 9 | Ex. 12 | Ex. 3 | Comparative Ex. 10 | Ex. 4 | Comparative Ex. 11 | Ex. 5 |
|---|---|---|---|---|---|---|---|---|---|---|---|---|
| Purified water | 72.3775 | | | | | 72.3175 | | | 72.2675 | | 72.2175 | |
| Others | 0.4325 | | | | | 0.4325 | | | 0.4325 | | 0.4325 | |
| Total [parts by mass] | 100 | | | | | 100 | | | 100 | | 100 | |
| A:B [mass ratio] | 1.6:1 | | | | | 2:1 | | | 7:3 | | 8:3 | |
| Mixing temperature [° C.] | 16.1 | 21.9 | 17.0 | 12.7 | 9.4 | 25.8 | 21.4 | 12.9 | 27.1 | 13.3 | 27.1 | 13.2 |
| Spread unevenness of the adhesive layer | 1 | 0 | 0 | 0 | 0 | 1 | 0 | 0 | 1 | 0 | 1 | 0 |
| Seepage of the adhesive layer | 0 | 0 | 0 | 0 | 0 | 0 | 0 | 0 | 0 | 0 | 0 | 0 |

Ex: Example

As shown in Table 4, in the cooling sheets (for example, Examples 1, 3 to 5, 9 to 12) of the present invention obtained by molding the adhesive layer composition obtained with specific compositions and conditions, it was confirmed that even though the water content is 69% by mass or more, which was sufficiently high, occurrence of spread unevenness of the adhesive layer was sufficiently suppressed, and seepage of the adhesive layer into the backing layer was also sufficiently suppressed over a long period of time. On the other hand, in the cooling sheets (Comparative Examples 8 to 11) obtained by molding adhesive layer compositions whose mixing conditions for the compositions to be mixed were out of the ranges of the specific conditions according to the present invention, it was confirmed that the evaluation result of at least spread unevenness of the adhesive layer was not sufficient.

Examples 13 to 14

Each cooling sheet was obtained in the same manner as in Example 1 except that the amount of partially neutralized sodium polyacrylate was changed and the composition of each composition to be mixed was changed to the composition shown in Table 5 given below.

In each of Examples 13 to 14, the test (1) was conducted on the obtained adhesive layer composition, and the tests (2) to (3) were conducted on the obtained cooling sheet. The composition of each composition to be mixed (that is, the composition of the adhesive layer composition, the composition of the adhesive layer) as well as the results of the respective tests (1) to (3) are shown in Table 5 given below, in addition, the values of Example 1 are also shown together in Table 5.

As shown in Table 5, in the cooling sheets (for example, Examples 1, 13 to 14) of the present invention obtained by molding the adhesive layer composition obtained with specific compositions and conditions, it was confirmed that even though the water content was 69% by mass or more, which was sufficiently high, occurrence of spread unevenness of the adhesive layer was sufficiently suppressed, and occurrence of seepage of the adhesive layer into the backing layer was also sufficiently suppressed over a long period of time.

Comparative Examples 12 to 15

Each cooling sheet was obtained in the same manner as in Example 1 except that gelatin (Comparative Examples 12, 34) or xanthan gum (Comparative Examples 13, 15) was used instead of a polyacrylic acid or a partially neutralized sodium polyacrylate.

In each of Comparative Examples 12 to 35, the test (1) was conducted on the obtained adhesive layer composition, and the tests (2) to (3) were conducted on the obtained cooling sheet. The composition of each composition to be mixed (the composition of the adhesive layer composition, the composition of the adhesive layer) as well as the results of the respective tests (1) to (3) are shown in Table 6 given below. Note that in Comparative Example 14, the hardness of the adhesive layer composition was too low to evaluate the spread unevenness in the (2).

TABLE 5

| | Example 13 | Example 1 | Example 14 |
|---|---|---|---|
| Polyvinyl alcohol | 4.00 | 4.00 | 4.00 |
| Polyacrylic acid | 1.92 | 1.92 | 1.92 |
| Partially neutralized sodium polyacrylate | 3.50 | 4.58 | 7.00 |
| Concentrated glycerin | 15.00 | 15.00 | 15.00 |
| Sodium carboxymethyl cellulose | 1.00 | 1.00 | 1.00 |
| (A) Potassium aluminium sulfate | 0.24 | 0.24 | 0.24 |
| (B) Sodium edetate | 0.15 | 0.15 | 0.15 |
| Polyethylene glycol monooleate (6EO) | 0.30 | 0.30 | 0.30 |
| Purified water | 73.4575 | 72.3775 | 69.9575 |
| Others | 0.4325 | 0.4325 | 0.4325 |
| Total [parts by mass] | 100 | 100 | 100 |
| A:B [mass ratio] | 1.6:1 | 1.6:1 | 1.6:1 |
| Mixing temperature [° C.] | 12.7 | 12.7 | 11.4 |
| Spread unevenness of the adhesive layer | 6 | 0 | 0 |
| Seepage of the adhesive layer | 0 | 0 | 0 |

TABLE 6

|  | Comparative Example 12 | Comparative Example 13 | Comparative Example 14 | Comparative Example 15 |
|---|---|---|---|---|
| Polyvinyl alcohol | 4.00 | 4.00 | 4.00 | 4.00 |
| Polyacrylic acid | — | — | 1.92 | 1.92 |
| Partially neutralized sodium polyacrylate | 4.58 | 4.58 | — | — |
| Gelatin | 1.92 | — | 4.58 | — |
| Xanthan gum | — | 1.92 | — | 4.58 |
| Concentrated glycerin | 15.00 | 15.00 | 15.00 | 15.00 |
| Sodium carboxymethyl cellulose | 1.00 | 1.00 | 1.00 | 1.00 |
| (A) Potassium aluminium sulfate | 0.24 | 0.24 | 0.24 | 0.24 |
| (B) Sodium edetate | 0.15 | 0.15 | 0.15 | 0.15 |
| Polyethylene glycol monooleate (6EO) | 0.30 | 0.30 | 0.30 | 0.30 |
| Purified water | 72.3775 | 72.3775 | 72.3775 | 72.3775 |
| Others | 0.4325 | 0.4325 | 0.4325 | 0.4325 |
| Total [parts by mass] | 100 | 100 | 100 | 100 |
| A:B [mass ratio] | 1.6:1 | 1.6:1 | 1.6:1 | 1.6:1 |
| Mixing temperature [° C.] | 14.8 | 12.2 | 11.6 | 11.4 |
| Spread unevenness of the adhesive layer | 1 | 1 | — | 1 |
| Seepage of the adhesive layer | 0 | 0 | 4 | 0 |

As shown in Table 6, in the cooling sheets (Comparative Examples 12 to 15) obtained by using other water-soluble polymers instead of a polyacrylic acid or a neutralized polyacrylic acid, it was confirmed that particularly the evaluation result of spread unevenness of the adhesive layer was not sufficient, and further that in the case of using gelatin instead of a neutralized polyacrylic acid (Comparative Example 14), the evaluation result of seepage of the adhesive layer into the backing layer was not sufficient.

INDUSTRIAL APPLICABILITY

As described above, the present invention makes it possible to provide a method for producing an adhesive layer composition that allows the production of a cooling sheet of a type in which a water-soluble polymer, water, and the like are blended in an adhesive layer which comes into direct contact with an applied site, the cooling sheet having a sufficiently high water content and allowing occurrence of spread unevenness and seepage of the adhesive layer to be sufficiently suppressed, a method for producing a cooling sheet using the same, and a cooling sheet obtained by these.

The invention claimed is:
1. A method for producing an adhesive layer composition for producing a cooling sheet including a backing layer, an adhesive layer, and a liner layer, the method comprising the step of:
mixing a composition to be mixed containing water, an alum, sodium edetate, a polyacrylic acid, and a neutralized polyacrylic acid such that a mixing temperature becomes 5 to 23° C., to obtain an adhesive layer composition, wherein
in the composition to be mixed,
a content of the water is 69 to 98.24% by mass relative to a total mass of the composition to be mixed,
a content of the alum is 0.18 to 0.42% by mass relative to the total mass of the composition to be mixed,
a content of the sodium edetate is 0.08 to 0.18% by mass relative to the total mass of the composition to be mixed, and
a mass ratio between the content of the alum and the content of the sodium edetate (the content of the alum: the content of the sodium edetate) is 1:1 to 5.25:1.
2. The method for producing an adhesive layer composition for producing a cooling sheet according to claim 1, wherein
the composition to be mixed further contains a polyvinyl alcohol.
3. The method for producing an adhesive layer composition for producing a cooling sheet according to claim 1, wherein
the composition to be mixed further contains sodium carboxymethyl cellulose.
4. The method for producing an adhesive layer composition for producing a cooling sheet according to claim 1, wherein
in the composition to be mixed,
a content of the neutralized polyacrylic acid is 1 to 10% by mass relative to the total mass of the composition to be mixed.
5. A method for producing a cooling sheet including a backing layer, an adhesive layer, and a liner layer, the method comprising the steps of:
obtaining an adhesive layer composition by the production method according to claim 1; and
molding the adhesive layer composition to obtain the adhesive layer, wherein
the adhesive layer contains water, an alum, sodium edetate, a polyacrylic acid, and a neutralized polyacrylic acid, and
in the adhesive layer,
a content of the water is 69 to 98.24% by mass relative to a total mass of the adhesive layer,
a content of the alum is 0.18 to 0.42% by mass relative to the total mass of the adhesive layer,
a content of the sodium edetate is 0.08 to 0.18% by mass relative to the total mass of the adhesive layer, and
a mass ratio between the content of the alum and the content of the sodium edetate (the content of the alum: the content of the sodium edetate) is 1:1 to 5.25:1.

6. The method for producing a cooling sheet according to claim 5, wherein
a mass of the adhesive layer is 1,500 to 2,300 g/m².

7. A cooling sheet comprising a backing layer, an adhesive layer, and a liner layer, wherein
the adhesive layer contains water, an alum, sodium edetate, a polyacrylic acid, and a neutralized polyacrylic acid, and
in the adhesive layer,
a content of the water is 69 to 98.24% by mass relative to a total mass of the adhesive layer,
a content of the alum is 0.18 to 0.42% by mass relative to the total mass of the adhesive layer,
a content of the sodium edetate is 0.08 to 0.18% by mass relative to the total mass of the adhesive layer, and
a mass ratio between the content of the alum and the content of the sodium edetate (the content of the alum: the content of the sodium edetate) is 1:1 to 5.25:1, and
a mixing temperature of an adhesive layer composition from which the adhesive layer is formed is 5 to 23° C.

8. The cooling sheet according to claim 7, wherein
the adhesive layer further contains a polyvinyl alcohol.

9. The cooling sheet according to claim 7, wherein
the adhesive layer further contains sodium carboxymethyl cellulose.

10. The cooling sheet according to claim 7, wherein a mass of the adhesive layer is 1,500 to 2,300 g/m².

* * * * *